United States Patent [19]
Dudley

[11] Patent Number: 5,783,758
[45] Date of Patent: Jul. 21, 1998

[54] LIQUID SAMPLING APPARATUS FOR CONDUIT LIQUID FLOW

[75] Inventor: Lynn A. Dudley, Chino, Calif.

[73] Assignee: Vortox Company, Claremont, Calif.

[21] Appl. No.: 599,815

[22] Filed: Feb. 12, 1996

[51] Int. Cl.[6] .................................................. G01N 1/20
[52] U.S. Cl. ...................... 73/863.52; 73/863.81
[58] Field of Search .................... 73/863.52, 863.81

[56] References Cited

U.S. PATENT DOCUMENTS

| | | |
|---|---|---|
| 3,826,144 | 7/1974 | Wessels. |
| 3,962,922 | 6/1976 | Takeuchi .................... 73/215 X |
| 4,279,148 | 7/1981 | Fitzgerald ...................... 73/215 |
| 4,467,645 | 8/1984 | Murphree ...................... 73/215 |
| 4,762,009 | 8/1988 | Scrudto ....................... 73/863.52 |
| 4,958,528 | 9/1990 | Garrison ...................... 73/864.63 |
| 5,069,878 | 12/1991 | Ehrenkranz ............... 73/863.52 X |
| 5,156,489 | 10/1992 | Replogle ..................... 73/215 X |
| 5,186,052 | 2/1993 | Gray ............................. 73/215 |
| 5,220,825 | 6/1993 | Petersen et al. ........... 73/863.01 |
| 5,279,151 | 1/1994 | Coody et al. ............. 73/863.52 X |
| 5,347,877 | 9/1994 | Gadbois ..................... 73/863.52 |
| 5,408,892 | 4/1995 | Kawanami et al. ..... 73/864.31 X |
| 5,587,539 | 12/1996 | Carpenter ................. 73/863.52 |

FOREIGN PATENT DOCUMENTS 1220175  6/1966  Germany .............................. 73/863.52

OTHER PUBLICATIONS

Water Resources Research publication, article "Development of a Self-Sealing Rain Sampler for Arid Zones", by E. Adar et al, pp. 592–596, vol. 16, No. 3, Jun. 1980.

*Primary Examiner*—Thomas P. Noland
*Attorney, Agent, or Firm*—Boniard I. Brown

[57] ABSTRACT

Liquid flowing through a conduit is sampled for analysis by positioning within the conduit a removable liquid sampling device having a liquid sample collection chamber and an inlet to the chamber opening to the interior of the conduit below the liquid level in the conduit such that liquid enters the chamber from the conduit, and when the collection chamber contains a liquid sample of desired volume, removing the sampling device from the conduit for shipment to a laboratory where the collected sample is analyzed. Wet season and dry season water sampling embodiments of the invention are described for sampling water within a storm drain system during high water flow wet seaons and low water flow dry seasons to monitor for the presence of and to locate the sources of toxic substances and other contaminants in the water.

39 Claims, 3 Drawing Sheets

LIQUID SAMPLING APPARATUS FOR CONDUIT LIQUID FLOW

RELATED APPLICATIONS

Reference is made to my copending applications Ser. No. 08/421,474 filed Apr. 12, 1995, and Ser. No. 08/589,719 filed Jan. 22, 1996.

BACKGROUND OF THE INVENTION

1. Field of the invention

This invention relates generally to the art of sampling liquids for analysis and more particularly to a novel liquid sampling method and apparatus for sampling liquid within a liquid receiver, especially water within a storm drain system.

2. Discussion of the Prior Art

As will become readily evident from the ensuing description, the liquid sampling method and apparatus of this invention may be utilized for a variety of liquid sampling purposes. However, the invention intended primarily for sampling liquid flowing through a conduit which may be either an open channel or a closed pipe and more particularly for sampling water within the conduits or pipes of industrial and municipal storm drain systems in order to monitor for the presence of toxic substances and other contaminants in the water. The invention will be described primarily in this context.

Municipal storm drain systems generally discharge into large public water bodies such as lakes, rivers, and the like and, in the case of California, into the San Diego, Santa Monica, and San Francisco bays. The water in such storm drain systems often contains toxic substances and other contaminants which are carried with the water to and pollute the receiving water body. Much of this contamination is created by deliberate illegal dumping of industrial waste products and the like into the storm drain systems in order to avoid the time, costs, and problems associated with legal disposition of such waste products.

Another extensive source of such contamination is storm water runoff from industrial property. In this regard, the ground, floors, and other exterior surfaces of industrial properties are often contaminated by a variety of industrial substances due spillage during handling of the substances, leakage from equipment, storage drums, pipe lines and the like, and hosing of interior surfaces onto exterior surfaces. During a rainstorm, these substances are entrained in the storm water runoff from the properties and carried with the runoff into the local municipal storm drain systems.

Attempts have been made to reduce such storm water runoff pollution from industrial property. The state of California, for example, has passed legislation establishing a program entitled the Industrial Storm Water Permitting Program. This program requires industrial property owners to obtain a permit, called a General Industrial Storm Water Permit, for storm water runoff or discharge from their properties into their municipal storm drain systems. These permits are issued through the State Water Resources Control Board.

Unfortunately, compliance with these programs is tedious, time consuming, and costly. Obtaining a General Industrial Storm Water Permit in California, for example, involves the payment of an annual fee and the performance by each applicant, referred to as a discharger, of certain obligations. These obligations include: (a) preparing a site map of the property in question, starting with the roof of each building on the property, showing the flow path of storm water runoff from the roof to the ground, then across the ground onto the storm water drainage system on the property, and then from the property drainage system into the public storm drain system; (b) visual observation of storm water discharge from the property during both the wet season (October through April) and the dry season (May through September); (c) submission of an estimate or calculation of the storm water discharge volume during two significant storm events in the wet season; (d) submission of a proposed storm water sampling program; (e) execution of the approved storm water sampling program in compliance with the state regulations to obtain certain storm water sample; and (f) submission of the storm water samples for analysis. These storm water samples must be taken in a manner which complies with certain rigorous and complicated requirements of the Storm Water Permitting Program. As a consequence, there is a great temptation for industrial property owners to ignore or comply only partially with the local program requirements.

One important use of the liquid sampling method and apparatus of this invention involves monitoring for the presence of contaminants at various locations within a municipal storm drain system, not only to determine the presence of any contaminants in the water flowing through the systems but, more importantly, to aid in locating the source of any contamination present in the water. Another use of the invention involves sampling storm water runoff from industrial properties and the like in order to comply with the California Industrial Storm Water Permitting Program or similar programs in other states. The invention will be described in connection with these uses. As mentioned earlier, however, the invention is capable of various other liquid sampling purposes.

A variety of liquid sampling methods and devices are known in the prior art. Included in this prior art are the following: U.S. Pat. No. 3,826,144, dated Jul. 30, 1974, to Wessels; U.S. Pat. No. 3,962,973, dated Jun. 15, 1976, to Takeuchi; U.S. Pat. No. 4,279,148, dated Jul. 21, 1981, to Fitzgerald; U.S. Pat. No. 4,467,645, dated Aug. 28, 1984, to Murphree; U.S. Pat. No. 4,762,009, dated Aug. 9, 1988, to Scrudto; U.S. Pat. No. 4,958,528, dated Sep. 25, 1990 to Garrison; U.S. Pat. No. 5,069,878, dated Dec. 3, 1991, to Ehrenkranz; U.S. Pat. No. 5,156,489, dated Oct. 20, 1992, to Replogle; U.S. Pat. No. 5,186,052, dated Feb. 16, 1993, to Gray; U.S. Pat. No. 5,220,825, dated Jun. 22, 1993, to Peterson et al; U.S. Pat. No. 5,279,151, dated Jan. 18, 1994, to Coody et al; U.S. Pat. No. 5,347,877, dated Sep. 20, 1994, to Gadbois; U.S. Pat. No. 5,408,892, dated Apr. 25, 1995, to Kawanami et al; Article entitled "Development of a Self-Sealing Rain Sampler for Arid Zones" by E. Adar et al, pages 592–596, vol 16, No. 3, June 1980, of publication entitled "Water Resources Research" describing a rain sampler.

SUMMARY OF THE INVENTION

The liquid sampling apparatus of this invention comprises a sample collection device proper, hereafter referred to simply as a sampling device, and a supporting base for supporting the sampling device in a fixed sampling position. The sampling device has inlet means including a liquid inlet through which liquid may enter the sampling device and a sample collection chamber for receiving liquid entering the inlet. This inlet means of the preferred inventive embodiments described herein includes inlet valve means like that embodied in the sampling devices of the above mentioned copending applications for closing the liquid inlet except when the inlet is submerged in liquid being sampled and the sample collection chamber is not filled.

In use, the sampling apparatus is mounted in a sampling position wherein the inlet of the sampling device is disposed to receive the liquid to be sampled. When sampling a liquid flowing through a conduit, this involves mounting the sampling apparatus in a fixed sampling position within the conduit by anchoring the supporting base of the apparatus to the conduit wall with the inlet of the apparatus opening upwardly to the interior of the conduit at a level which is at least slightly below the level or anticipated level of liquid within the conduit and with the collection chamber of the apparatus located at a lower level than the inlet. Liquid flowing through the conduit at this level or a higher level thus enters the collection chamber. When the desired liquid sample has been collected, the sampling device is removed from the conduit and sent to a laboratory where the collected liquid sample is analyzed. According to one feature of the invention, the sampling device is removably secured to the supporting base, and the base includes means for anchoring it to the conduit wall in such a way that the sampling device may be removed from the base for analysis of the collected sample while the base remains at the sample collection site for reuse with another sampling device.

Two presently preferred embodiments of the invention are described, both intended for sampling water flowing through a conduit of a storm drain system to monitor for contaminants in the water. This storm drain conduit may be either a closed pipe or an open channel. One of these described embodiments is designed for use during the wet season (October through April) when the average water level in a storm drain conduit is relatively high. The supporting base of this embodiment has a relatively fixed part which is anchored to the conduit wall and an adjustable part which removably mounts the sampling device. This adjustable part is vertically adjustable relative to the fixed base part to locate the inlet of the sampling device at different levels within the conduit depending on the average water level in the conduit so that water flowing through the conduit will enter the sampling device when the water is at its average level or higher. The other described embodiment of the invention is designed for use during the dry season (May through September) when the average water level in a storm drain conduit is relatively low. The supporting base of this embodiment includes a dam which extends across a lower portion of the conduit and has means about its edge for sealing the dam to the conduit wall. The sampling device is mounted on the dam with its inlet located at the upstream side of the dam relative to the direction of water flow through the conduit and at a lower level than the upper edge of the dam. During the dry season, any water flowing through the conduit will back up behind the dam until the water level rises to the level of the upper edge of the dam and hence to a higher level than the inlet of the sampling device. At this point, the water will overflow the dam and enter the inlet of the sampling device.

The inlet means of both described embodiments include the inlet valve means mentioned above which close the inlet of the sampling device except when the inlet is submerged in water and the sample collection chamber is not filled. This valve means seals the inlet until the water level in the conduit rises above and hence covers the inlet in order to seal the inlet against entrance of dirt and other foreign material into the collection chamber. The inlet valve means then remains open to permit water flow into the collection chamber as long as the water level in the conduit remains above the level of the inlet and until the collection chamber is filled to a certain level. The inlet valve means recloses in response to either or both dropping of the water level below the inlet and filling of the collection chamber with a certain volume of water referred to herein as its "filled volume".

According to another aspect of the invention, a source of contamination in a storm drain system is located by placing liquid sampling apparatuses according to the invention at selected locations within the system, periodically moving them from one location to another in the system, and checking the water samples collected at each location for contamination, all in such a way as to progressively narrow the possible location of the contamination source to a smaller and smaller area until the source is located.

The liquid sampling apparatus of the invention may also be used by the owner of an industrial property to monitor storm water run off from his property or to obtain the storm water run off samples required under the storm water runoff permitting programs mentioned earlier. Other possible uses of the sampling apparatus will become evident to those versed in the art as the description proceeds.

DESCRIPTION OF THE PREFERRED EMBODIMENTS

Referring now to these drawings and first to FIGS. 1–8, there is illustrated a liquid sampling apparatus 10 according to the invention mounted in a fixed sampling position in a liquid receiving space 12 within a liquid receiver 14 to collect a sample of liquid 16 entering the space. The sampling apparatus 10 includes a sample collection device, i.e. sampling device, 18 proper and a supporting base 20 for supporting the sampling device in its sampling position within the liquid receiver 14. The sampling device 18 has an inlet means 22 containing an inlet passage 24 through which the liquid 16 may enter the device and a sample collection chamber 26 which receives liquid entering through this passage. Included in the inlet means 22 are inlet float valve means 28 similar to the inlet float valve means in my earlier mention copending application 08/421,474 for closing the inlet passage 24 except when both of the following conditions exist: (a) the upper inlet of the inlet passage 24 is submerged in the liquid 16 to be sampled, and (b) the collection chamber 26 contains less than a certain maximum liquid volume, referred to herein as its "filled volume".

The liquid sampling apparatus 10 remains quiescent in its sampling position within the liquid receiving space 12 with the inlet passage 24 of its liquid sampling device 18 closed by the inlet valve means 22 against the entrance of dirt and other foreign matter into its empty collection chamber 26 until the liquid level in the space rises at least a small distance above the upper inlet of the inlet passage 24. At this point, the inlet valve means 28 opens to permit liquid flow through the inlet passage into the sample collection chamber 26. The passage remains open as long as the liquid level remains above the inlet and until the collection chamber contains its filled volume of liquid. The inlet valve means 28 then recloses the inlet passage 24 to seal the collected liquid sample in the collection chamber 26 for subsequent analysis in a laboratory.

As mentioned earlier, the present liquid sampling invention may be utilized for a variety of liquid sampling purposes involving the collection of liquid samples in a variety of liquid receivers. The invention is primarily concerned, however, with collecting samples of a liquid flowing through a conduit which may be either a closed pipe or an open channel. The drawings illustrate the primary intended use of the invention which is collecting water samples in a storm drain system 30 in order to monitor for toxic substances and other contaminants in the water due to illicit dumping of toxic industrial waste into the system, storm water run off from industrial property, and other causes.

With the foregoing in mind, the liquid receiver 14 illustrated in FIGS. 1–8 is a subterranean drain conduit or pipe of a conventional storm drain system 30. The overall storm drain system includes curb side drain openings, grilled drain openings, and the like (not shown) in public steets and other public places through which rain water and water from hoses, lawn sprinklers and other sources enters the system. Located at intervals about the system are manholes 32 (only one shown) which are normally closed by a removable manhole cover (not shown) and open to the drain pipe 14. Fixed to the wall of this manhole are rungs 34 by which a person may climb downwardly in and upwardly from the manhole. The water sampling apparatus 10 of this invention, hereafter referred to in places as a storm water sampler or simply a sampler, is positioned in the drain pipe 14 within reach from the manhole 32 to sample water flowing through the pipe.

Referring now in more detail to the illustrated storm water sampler 10, its sampling device 18 comprises a relatively long tubular tank 36 which is closed at its ends and whose interior forms the sample collection chamber 26. At one end of this sample collection tank is a lateral opening 38 through one side of the tank. This side of the tank is its upper side in the illustrated normal sampling position of the water sampler. The inlet means 22 is removably mounted on this end of the sample collection tank 35 with the inlet means depending downwardly through the opening 38 into the sample collection chamber 26.

Figure 1:
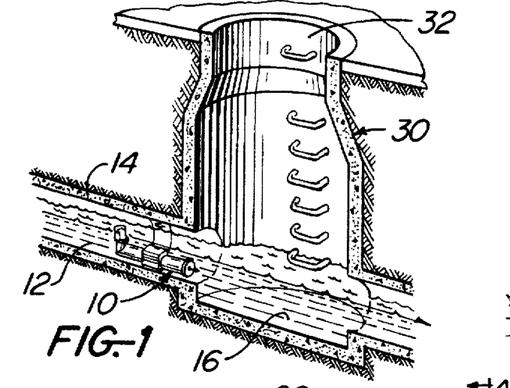
FIG. 1 is a section in perspective through a storm drain conduit illustrating a sampling apparatus according to the invention in sampling position within the conduit for sampling water flowing the conduit during wet seasons.
Figure 2:
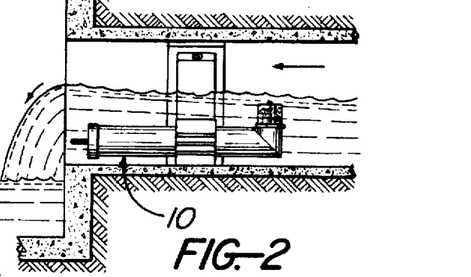
FIG. 2 is an enlarged fragmentary view of the storm drain conduit and sampling apparatus in FIG. 1 showing the conduit in vertical section and the sampling apparatus in side elevation as viewed from the distal side of the sampling apparatus in FIG. 1.
Figure 3:
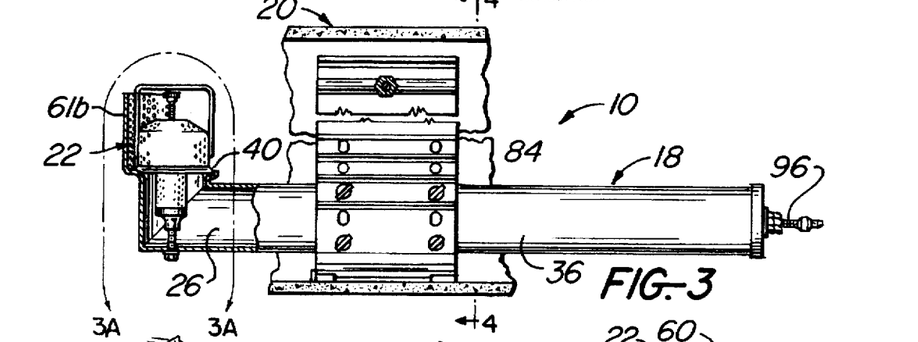
FIG. 3 is a further enlarged fragmentary showing of the storm drain conduit and sampling apparatus in FIG. 1 showing the conduit in vertical section and the sampling apparatus in side elevation as viewed from the proximal side of the sampling apparatus in FIG. 1.
Figure 3A:
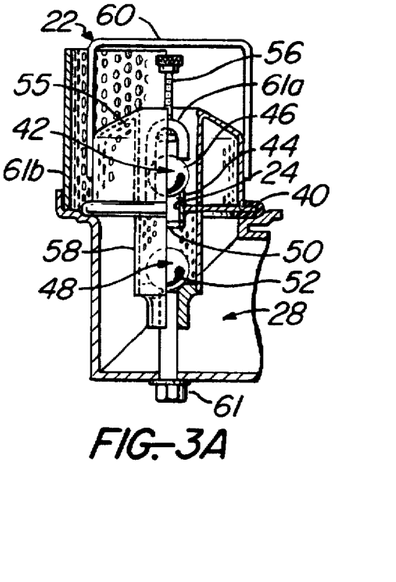
FIG. 3A is an enlargement in vertical section of the area encircled by the arrow 3A—3A in FIG. 3.
Figure 4:
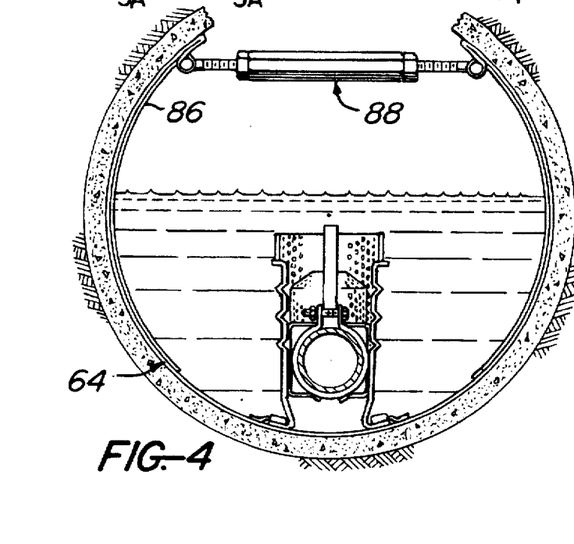
FIG. 4 is an enlarged section taken on line 4—4 in FIG. 3.

Turning to FIG. 3A, the inlet means 22 comprises an inlet assembly including a circular base plate 40 through the center of which extends the inlet passage 24 of the inlet means. At the upper side of the plate 40 is an upper float valve means 42 including an upper, upwardly facing valve seat 44 on the plate about the inlet passage and an upper float valve member in the form of float ball 46. This upper ball is movable downwardly into contact with the valve seat 44 to close the inlet passage 24 and upwardly away from the valve seat to open the passage. At the lower side of the base plate 40 is a lower float valve means 48 including a lower, downwardly facing valve seat 50 on the plate about the inlet passage and a lower float valve member in the form of float ball 52. The lower ball is movable upwardly into contact with the lower valve seat to close the inlet passage 24 and downwardly away from the lower valve seat to open the passage.

Mounted on the upper side of the base plate 40 is a perforate cage 54 which encloses and confines the upper float ball 46 and is enclosed, in turn, by a screen 55. A stop screw 56 threaded in the upper end of the screen 55 limits the maximum separation of the upper ball from its valve seat 44 and is adjustable to adjust this maximum separation. Mounted on the lower side of the base plate 40 is a perforate cage 58 which encloses and confines the lower float ball 52. Attached to the upper screen 55 is a handle 60 by which the inlet assembly 22 may be held.

The inlet assembly 22 is positioned on the normally upper side of the sample collection tank 36 with the base plate 40 of the inlet assembly seating on and sealed by a seal ring (not shown) to the tank wall about the upper tank opening 38. The lower cage 58 of the inlet assembly depends into the sample collection chamber 26. The inlet assembly is releasably secured to the sample collection tank 36 by a bolt 61 which extends upwardly through the bottom of the tank and is threaded in the lower end of the lower cage. The inlet means is removable for cleaning the tank and replacing the inlet means if damaged. The top of the collection chamber 26 is vented through an upstanding vent tube 61a fixed to the base plate 40 and having a downwardly curved upper end which opens to atmosphere.

As explained later, the storm water sampler 10 is installed in the storm drain conduit or pipe 14 with the sample collection tank 36 extending lengthwise of the pipe and with the tank inlet means 22 at the upstream end of the tank relative to the direction of flow through the pipe. In the drawings, this flow direction is to the right in FIG. 1 and to the left in FIG. 2. Fixed to upper side of the tank upstream of the inlet means 22 is a rigid upstanding perforated shield 61b which prevents solid objects carried through the pipe by the water from striking and damaging the upper inlet cage 54.

The supporting base 20 of the water sampler 10 comprises a support 62 which directly supports the sampling device 18 and a clamp 64 which engages the wall of the conduit or drain pipe 14 to releasably secure the sampler in its fixed sampling position within the pipe. As explained below, the support 62 is vertically adjustable to adjust the sampling device 18 vertically within the pipe 14 and thereby adjust the level of the upper inlet of the inlet passage 24 within the pipe.

The base support 62 comprises a pair of fixed parts in the form of parallel side plates 66 and an adjustable part 67 between and secured to the plates. The side plates have normally upper and lower edges, confronting normally inner sides and opposite outer sides, and out-turned flanges 68 along their lower edges. Between their upper and lower edges, these plates have generally V-shaped bends which form, at the inner confronting sides of the plates, V-shaped grooves 70 parallel to the upper and lower plate edges. The adjustable support part 67 comprises a clamp 71 similar to a conventional hose clamp and including a split circular sleeve 72 which encircles and has a normal inner diameter approximating the outer diameter of the sample collection tank 36. Along opposite sides of the split in the sleeve 72 are upstanding flanges 73 joined by a bolt 74 which can be loosened to permit axial insertion and removal of the sample collection tank into and from the sleeve and tightened to firmly clamp the tank in the sleeve. Welded or otherwise rigidly joined to opposite sides of the clamp sleeve 72 are channels 76 having web portions 78 which face outwardly toward the side plates 66. These web portions have V-shaped bends like those in the support side plates 66 which form, on the outer sides of the web portions, V-shaped ribs 80 parallel to and engagable in the V-shaped grooves 70 of the side plates to align the axis of the clamp sleeve 72 parallel to the upper and lower edges of the side plates.

Figure 5:
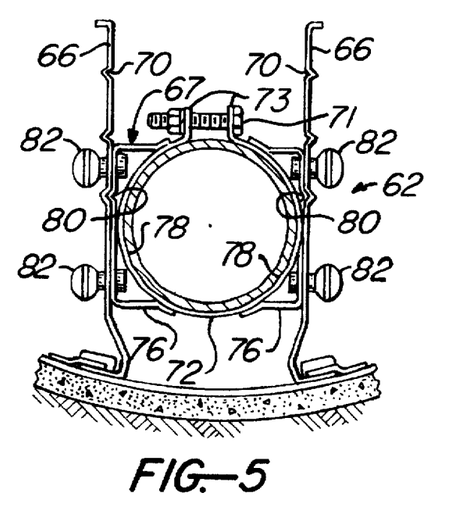
FIGS. 5–7 are enlarged vertical sections through the supporting base of the sampling apparatus in FIGS. 1–4.
Figure 6:
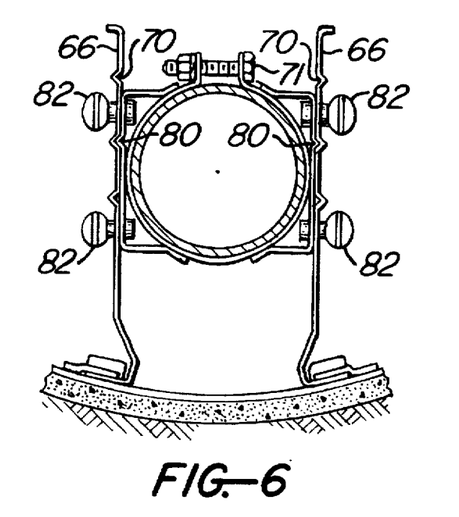
Figure 7:
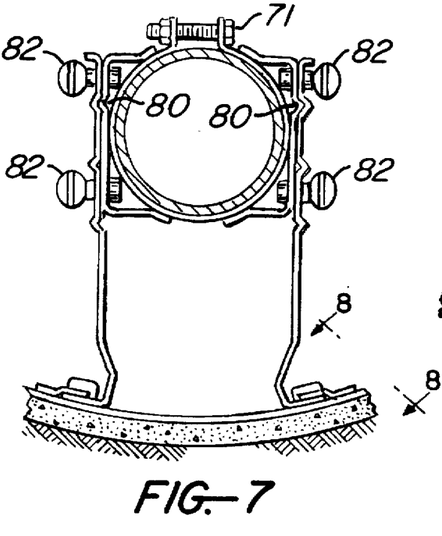
Figure 8:
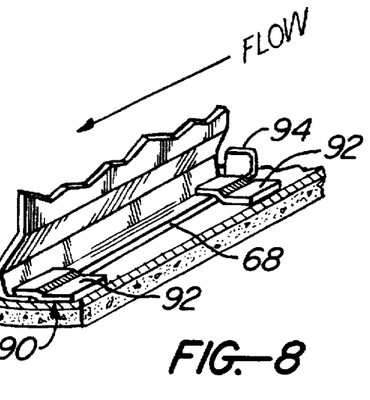
FIG. 8 is an enlarged view looking in the direction of the arrows on line 8—8 in FIG. 7.

As shown in FIGS. 5-7, the adjustable part 67 of the supporting base support 62 is adjustable to three different vertical positions relative to the side plates 66. In each of these adjusted positions, the ribs 80 on the adjustable part engage in corresponding grooves 70 in the side plates to align the axis of the clamp sleeve 72 parallel to the upper and lower edges of the plates. Thumb screws 82 are insertable through holes 84 in the side plates 66 and engagable in threaded holes in the channel webs 78 of the adjustable base part 67 to releasably secure this adjustable part in each of its adjusted positions.

The supporting base clamp 64 comprises a cylindrically curved, resiliently flexible clamp band 86 having free ends forming a normally upper gap in the band and joined by an adjustable turnbuckle 88. Clamp band 86 is curved to a diameter approximating the inner diameter of the conduit or drain pipe 14. The base support 62 is releasably secured by releasable attachment means 90 to the inner side of the clamp band 86 diametrically opposite its upper gap and turnbuckle 88 with the axis of its clamp sleeve 72 parallel to the axis of curvature of the band and transverse to plane of the space bounded and surrounded by the band. As shown best in FIG. 8, attachment means 90 comprises clips 92 welded or otherwise rigidly joined to the inner side of the clamp band under which the flanges 68 along the lower ends of the support plates 66 are slidably engagable in a manner which permits removal of the base support 62 from and reattachment of the base support to the band. Flanges 68 have upturned ends 94 engagable with the adjacent clips 92 to position the base support 62 relative to the clamp band 86 in one direction along the axis of its clamp sleeve 72 and along the axis of curvature of the band.

The water sampler 10 is designed for use primarily during wet seasons (October through April) when there is a substantial water flow through a storm drain system. The water sampler is assembled with the sample collection tank 36 firmly clamped between its ends within the clamp sleeve 72 of the base support 62 and with this support attached by the clips 92 to the inner side of the clamp band 86. The assembled sampler is placed in its sampling position of FIGS. 1 and 2 within the drain pipe 14 wherein the clamp band 86 is coaxially disposed within the pipe, the gap and turnbuckle 88 of the clamp band are situated at the top of the pipe, the base support 62 is situated at the bottom of the pipe, and the sample collection tank 36 extends longitudinally through the pipe with its inlet means 22 located at the upstream end of the tank relative to the direction of flow through the pipe. The turnbuckle 88 is tightened, i.e. extended, to urge the clamp band 86 into firm clamping contact with the inner wall of the pipe and thereby firmly secure the sampler in fixed sampling position within the pipe.

The base support 62 is positioned within the clamp band 86 in such a way that the upstanding ends 94 of its side plate flanges 68 engage the attachment clips 92 at the upstream side of the clamp band to secure the base support and collection tank against downstream movement relative to the fixed clamp band by the force of the water flowing through the pipe. The adjustable part 67 of the base support 62 is vertically adjusted (FIGS. 5-7) relative to the support side plates 66 to locate the upper end or inlet of the collection tank inlet passage 24 at a desired sampling level within the pipe which may be slightly below the average water level in the pipe. Clamp bands 86 will be provided in a range of nominal diameters to fit conduits or pipes of different diameters.

The upper float valve ball 46 of the sample collection tank inlet valve means 28 remains in contact with its valve seat 44 to close the inlet passage 24 against the entrance of dirt and other foreign matter into the sample collection chamber 26 until the water level in the pipe 14 rises above the upper inlet of the passage. The ball 46 then floats upwardly out of contact with its valve seat to permit water flow through the passage 24 into the collection chamber 26 so long as the water level remains above the inlet and the sample collection chamber contains less than its filled volume of water. When the chamber is filled with this volume of water, the lower float valve ball 52 engages its valve seat 50 to seal the chamber against escape of the collected sample from the chamber and entrance of contaminants into the chamber. The water sampler 10 is then removed from the drain pipe 14, and its sample collection tank 36 is removed from its supporting base 20 and sent to a laboratory for analysis of the collected sample. The sample is drained from the tank for analysis through a valved fitting 96 at the end of the tank opposite its inlet means 22.

Figure 9:
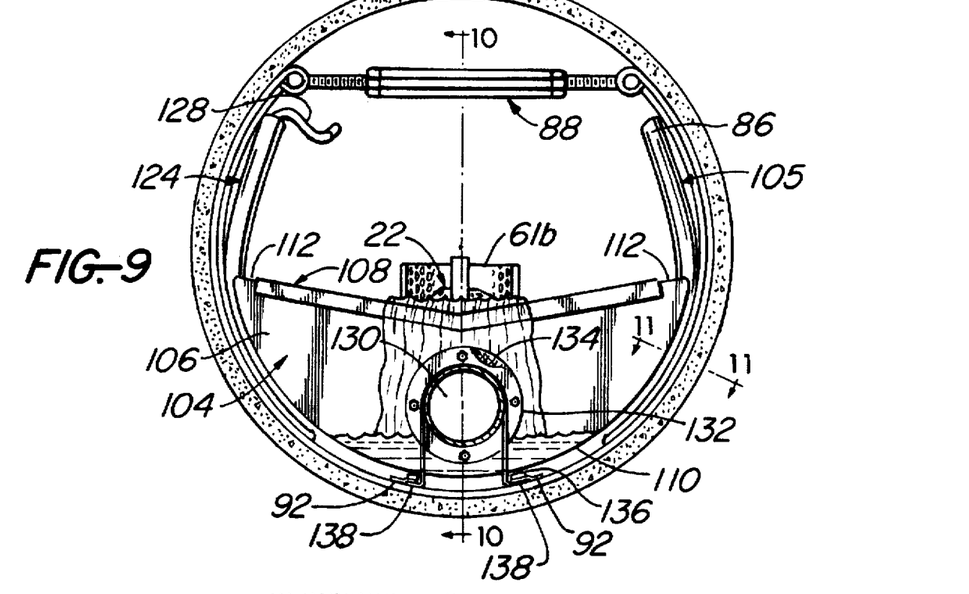
FIG. 9 is a vertical section similar to FIG. 4 showing a modified liquid sampling apparatus according to the invention in sampling position within the conduit for sampling water flow during the dry seasons.
Figure 10:
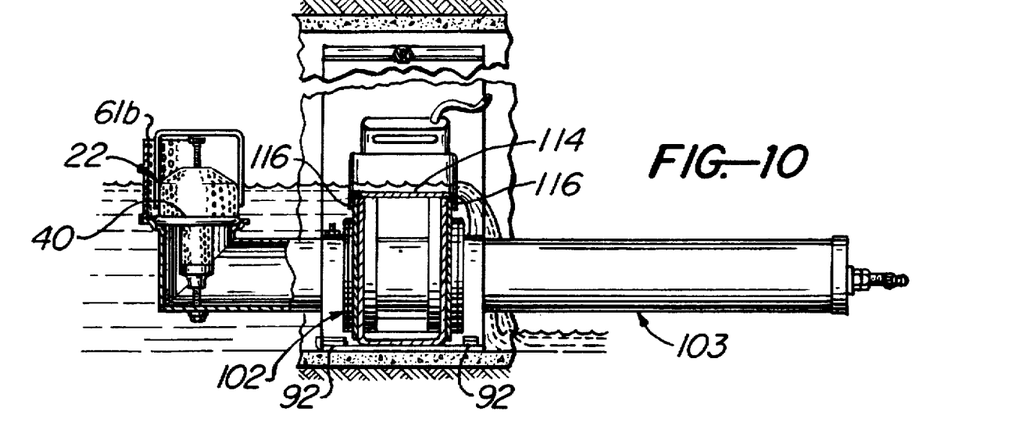
FIG. 10 is a section taken on line 10—10 in FIG. 9 showing the sampling apparatus in side elevation with parts sectioned for clarity.
Figure 11:
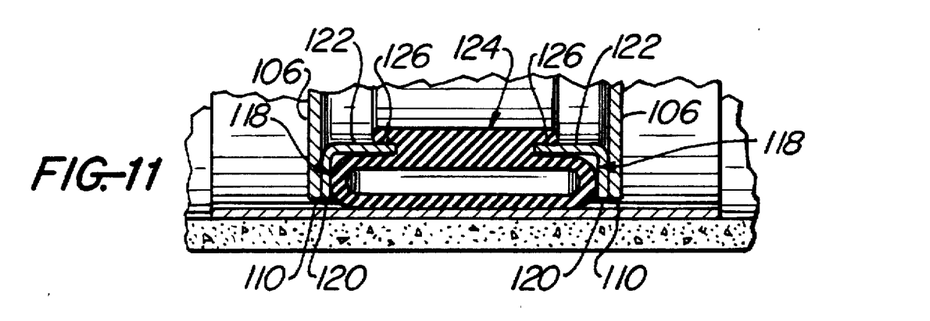
FIG. 11 is an enlarged section taken on line 11 in FIG. 10.

FIGS. 9-11 illustrate a modified liquid sample collection apparatus or water sampler 100 which is designed for use during the dry season (May through September) when the water flow through a storm drain system is relatively small. This dry season sample is similar in many respects to the wet season sampler 10. The dry season sampler differs from the wet season sampler primarily by the fact that the dry season sampler includes a dam downstream of the sampler inlet to the sample collection chamber which extends across a lower portion of the conduit or drain pipe in which the sampler is installed. This dam blocks water flow through the pipe until the water level behind (i.e. upstream of) the dam rises to the level of the sampler inlet in order to permit collection of water samples during the dry season when the highest water level in the pipe may be too low to permit use of the wet season sampler 10.

The modified water sampler 100 of FIGS. 9-11 includes a supporting base 102 to be fixed within the storm drain pipe 24 and a liquid sampling device 103 supported on this base which is identical in every respect to the sampling device 18 in FIGS. 1-8. The supporting base 102 comprises a dam 104 and a supporting base clamp 105 which is identical to the supporting base clamp 64 in FIGS. 1-8. Accordingly, no separate detailed descriptions of the sampling device 103 or the supporting base clamp 105 of the water sampler 100 are necessary at this point. The parts of the sampling device 103 and supporting base clamp 105 of the dry season sampler 100 which are hereafter referred to are designated by the same reference numerals as the corresponding parts of the sampling device 18 and supporting base clamp 64 in FIGS. 1-8.

Dam 104 comprises a relatively fixed part including a pair of parallel, somewhat sector-shaped side plates 106 rigidly joined by a channel member 108. The side plates 106 have normally lower circularly curved edges 110 and slightly V-shaped normally upper edges 112. The channel member 108 has a web 114 which seats on and conforms to the V-shape of the upper edges 112 of the side plates 106 and depending flanges 116 along the edges of the web which overlap and are welded or otherwise rigidly joined to the upper edge portions of the side plate.

At the inner confronting sides of the dam side plates 106 are elongate angle members 118 which have an L-shape in transverse cross-section and extend along the full lengths of the circular side plate edges 110. One flange 120 of each angle member seats against and is welded or otherwise rigidly secured to the inner surface of its dam side plate 106 with the longitudinal edge of the flange flush with the respective arcuate plate edge 110. The other flanges 122 of the angle members 118 are cylindrically curved about the axis of curvature of the arcuate side plate edges 110 and open toward one another in coplanar relation.

Between and coextensive with the angle members 118 is an elongate, generally flat inflatable seal 124 having laterally opening grooves 126 along its longitudinal edges which receive the angle member flanges 122. The seal has an outer surface which is substantially flush with the circularly curved edges 110 of the dam side plates 106 and those of the angle member flanges 120 and is inflatable through an inflation tube 128 at one end of the seal to expand the seal outwardly beyond these edges.

The dam side plates 106 have generally centrally located coaxially aligned circular holes 130. Bolted to the outer sides of the plates 106 coaxially with the holes 130 are annular collars 132 and intervening annular gaskets 134 which seal the collars to the plates. The collars 132 and the gaskets 134 have circular openings coaxially aligned with the side plate holes 130, and these holes and openings are sized to snugly but removably receive the sample collection tank 36 of the liquid sampling device 18. Extending over and firmly fixed to the collars 132 are inverted generally U-shaped anchor straps 136 having lower out-turned ends 138.

The supporting base clamp 105 of the dry season sampler 100 includes a circularly curved clamp band 86 having normally upper free ends joined by a turnbuckle 88. The clamp band has a radius of curvature approximating that of the pipe 14 in which the sampler 100 is to be placed and is expandable by extension of the turnbuckle 88 to secure the clamp 105 in a fixed position within the pipe. On the inner side of the clamp band 86 below the upper gap in the band and the turnbuckle 88 are clips 92. In the dry season sampler, the out-turned ends 138 of the anchor straps 136 engage under these clips, as shown in FIG. 9, to releasably secure the dam 104 to the clamp 64.

Except as explained below, the dry season water sampler 100 is installed in the storm drain pipe 14 and is used to collect samples of water flowing through the pipe all in the same way as described earlier in connection with the wet season sampler 10. The only differences between the installation and sample collection procedures of the dry season sampler and those of the wet season sampler are as follows. The wet season sampler 100 is inserted into the pipe 14 with its seal 124 deflated. The sampler 100 is placed in the pipe with its dam 104 situated within the lower portion of the pipe and with its inlet means 22 situated upstream of the dam relative to the direction of flow through the pipe. After the sampler 100 is properly placed in the pipe, the turnbuckle 88 of its supporting base clamp 64 is extended to expand the clamp band 86 outwardly against the wall of the pipe and thereby firmly secure the clamp band to the pipe. The seal 124 of the sampler 100 is then inflated through its inflation tube 128 to expand the seal outwardly against the clamp band 86 and thereby both secure and seal the dam 104 to the firmly anchored clamp band about the normally lower arcuate side of the dam.

The dam 104 of the sampler 100 blocks water flow through the drain pipe 14 until the water level behind the dam rises to the height of the dam after which the water overflows the dam as long as sufficient water flow through the pipe continues. The dam will then maintain a relatively constant water level behind the dam so long as sufficient water flow through the pipe continues. The water sampler 100 is constructed in such a way that the upper inlet of the inlet passage 24 to its sample collection chamber 26 is located at a slightly lower level than the upper side or edge of the dam 104, that is at a slightly lower level than the upper channel web 114 of the dam so that the water level behind the dam will reach the level of the inlet before the water overflows the dam. The water sampler 100 remains in its normal state with its inlet valve means 28 closed to seal the device against the entrance of dirt and other foreign matter into its sample collection chamber 26 until the water level behind the dam rises to the level of the inlet. The inlet valve means then opens to admit water into the collection chamber until the chamber is filled, whereupon the inlet valve means recloses to seal the chamber. The water sampler 100 is then removed from the pipe 14 and its collected sample is sent to a laboratory for analysis.

The clips 92 in the pipe 14 permit the wet season sampler and the dry season sampler to be easily interchanged for use of each during its respective sampling season. This interchange is accomplished by disengaging the sampler currently in the pipe from the pipe clips 92, engaging the other sampler with these clips, and deflating or inflating the seal 124 of the wet season sampler to remove or install this sampler, as the case may be. It is important to note here that the vent tube 61a of each sampler permits all of the air to be pushed from its collection chamber 26 during collection of a sample. This is important when testing for the presence of volatile components, such as volatile organic carbons, in a collected sample because accurate test results then requires that no air remain in the filled collection chamber, i.e. that the filled chamber have zero head space.

The inventor claims:

1. In combination:
   a liquid receiver having an interior liquid receiving space bounded by a wall,
   a liquid sampling apparatus disposed in a sampling position within said space,
   mounting means releasably securing said sampling apparatus to said wall to retain said apparatus in said sampling position within said space, and wherein
   said liquid sampling apparatus comprises inlet means including a liquid inlet opening to said liquid receiving space, and a sample collection chamber connected to said inlet means for receiving liquid entering through said inlet, and
   said mounting means is releasable to permit removal of said sampling apparatus from said liquid receiver for retrieving a liquid sample from the apparatus.

2. The combination according to claim 1 wherein:
   said liquid receiver is a liquid conduit having a passage which constitutes said liquid receiving space and through which a liquid may flow, said sampling apparatus is mounted within said passage, and said conduit surrounds said passage and constitutes said wall.

3. The combination according to claim 2 wherein:

said mounting means includes clamping means engagable with said conduit.

4. The combination of claim 2 wherein:

said conduit is a subterranean storm drain conduit.

5. The combination of claim 2 wherein:

said sampling apparatus includes a tank which is elongated longitudinally of said conduit and contains said sample collection chamber.

6. The combination of claim 5 wherein:

said mounting means comprises clamping means disposed circumferentially about said tank and adjustable laterally of said tank into,and from clamping engagement with said conduit.

7. The combination of claim 1 wherein:

said receiver is generally horizontal conduit through which liquid may flow in a certain direction, said sampling apparatus includes a dam extending across a lower portion of said conduit and having an upper edge at a certain level within the conduit over which water in the conduit may overflow the dam, and said inlet opens to the interior of said conduit upstream of said dam relative to said certain flow direction-through the conduit and at a lower level than said upper dam edge.

8. The combination according to claim 1 wherein:

said receiver is a generally horizontal conduit having a passage which constitutes said liquid receiving space and through which liquid flow occurs, and said conduit constitutes said wall, said sampling apparatus comprises a liquid sampling device and a supporting base supporting said sampling device, said sampling device includes said inlet and said sample collection chamber, and said supporting base includes a support mounting said sampling device and said mounting means for releasably securing said support in a fixed sampling position within said conduit.

9. The combination according to claim 8 wherein:

said conduit is generally horizontal, said supporting base comprises a dam extending across a lower portion of the interior of said conduit bounded by a lower portion of the conduit, said dam has an upper edge at a certain level within the conduit over which water in the conduit may overflow the dam, and an edge portion adjacent and facing said lower portion of said conduit, and sealing means about said edge portion sealing the dam to said lower conduit portion, said inlet opens to the interior of said conduit-upstream of said dam relative to said certain flow direction through the conduit and at a lower level than said upper dam edge, and said securing means secures said dam in a fixed position within said-conduit.

10. The combination according to claim 9 wherein:

said securing means comprises a clamp fixed to said dam and engaging said conduit.

11. The combination according to claim 9 wherein:

said conduit comprises a pipe, said clamp comprises a resiliently flexible clamp band which is cylindrically curved to a diameter approximating the inner diameter of said pipe and has free ends located opposite one another within an upper portion of said pipe, and means extending between said free band ends for urging said ends apart to urge said band into firm clamping engagement with the wall of said pipe, and said dam is fixed to said band.

12. The combination of claim 11 wherein:

said sampling device comprises an elongate sample collection tank containing said sample collection chamber, and inlet means at one end of said tank including an inlet passage communicating said inlet to said chamber, said dam has an opening parallel to the longitudinal axis of said pipe removably receiving said sample collection tank, and said sealing means comprises an elongate inflatable seal extending along and secured to said edge portion of said dam.

13. The combination of claim 1 wherein:

said space has a horizontal direction, and said sampling apparatus includes a tank which is horizontally elongated and contains said sample collection chamber.

14. The combination of claim 13 wherein:

said mounting means include wall engaging means disposed circumferentially about said tank and contacting said wall.

15. In combination:

a liquid receiver, a liquid sampling apparatus comprising inlet means including a liquid inlet opening to the interior of said receiver, and a sample collection chamber connected to said inlet means for receiving liquid entering through said inlet, and wherein said liquid receiver is a generally horizontal liquid conduit through which a liquid may flow, and said sampling apparatus includes means for adjusting the level of said inlet within said conduit.

16. The combination of claim 15 wherein:

said sampling apparatus is positioned within said conduit and includes means releasably securing said apparatus in a fixed sampling position within said conduit.

17. In combination:

a liquid receiver, a liquid sampling apparatus comprising inlet means including a liquid inlet opening to the interior of said receiver, and a sample collection chamber connected to said inlet means for receiving liquid entering through said inlet, and wherein said receiver is a generally horizontal conduit, said sampling apparatus comprises a liquid sampling device and a supporting base supporting said sampling device, said sampling device includes said inlet and said sample collection chamber, said supporting base includes a support mounting said sampling device, and securing means connected to said support for releasably securing said support in a fixed sampling position within said conduit, and said support is adjustable to adjust said sampling device up and down within said conduit.

18. In combination:

a liquid receiver, a liquid sampling apparatus comprising inlet means including a liquid inlet opening to the interior of said receiver, and a sample collection chamber connected to said inlet means for receiving liquid entering through said inlet, and wherein said receiver is a generally horizontal conduit, said sampling apparatus comprises a liquid sampling device and a supporting base supporting said sampling device, said sampling device includes said inlet and said sample collection chamber, said supporting base includes a support mounting said sampling device, and securing means connected to said support for releasably securing said support in a fixed sampling position within sad conduit, and said securing means comprises a clamp connected to said support and engagable with said conduit to firmly clamp said sampling apparatus in a fixed position within said conduit.

19. In combination:

a liquid receiver, a liquid sampling apparatus comprising inlet means including a liquid inlet opening to the interior of said receiver, and a sample collection chamber connected to said inlet means for receiving liquid entering through said inlet, and wherein said receiver is a generally horizontal conduit, said sampling apparatus comprises a liquid sampling deice and a supporting base supporting said sampling device, said sampling device includes said inlet and said sample collection chamber, said supporting base includes a support mounting said sampling device, and securing means connected to said support for releasably securing said support in a fixed sampling position within said conduit, said support includes means for adjusting said sampling device up and down within said conduit, and said securing means comprises a clamp connected to said support and engagable with said conduit to firmly clamp said sampling apparatus in a fixed position within said conduit.

20. The combination according to claim 19 wherein: said conduit comprises a pipe, and said clamp comprises a resiliently flexible clamp band cylindrically curved to a diameter approximating the inner diameter of said pipe and having free ends located opposite one another within the upper portion of said pipe, and means extending between said free band ends for urging said ends apart to urge said band into firm clamping engagement with said pipe, and said support includes a fixed part secured to said band between and below said band ends and an adjustable part mounting said sampling device for adjustment up and down relative to said fixed part.

21. The combination of claim 20 wherein:

said sampling device comprises an elongate sample collection tank containing said sample collection chamber, and inlet means at one end of said tank including an inlet passage communicating said inlet to said chamber, and said adjustable support part comprises split sleeve parallel to the axis of said pipe removably receiving said sample collection tank, and means for releasably clamping said tank in said sleeve.

22. Liquid sampling apparatus to be placed in a liquid receiving space bounded by a wall, comprising a supporting base including a relatively fixed part, means for releasable securing said fixed part to the wall of the liquid receiving space with the fixed part disposed in a normal position in which a certain direction of the fixed part is vertical, and an adjustable part mounted on said fixed part for adjustment in said certain direction relative to said fixed part, and a liquid sampling device mounted on said adjustable part for adjustment with said adjustable part in said certain direction relative to said fixed part and including liquid inlet means having a liquid inlet through which liquid may enter said sampling device, a sample collection chamber for receiving liquid entering through said inlet, and an inlet passage connecting said inlet and said chamber.

23. Liquid sampling apparatus comprising:

a supporting base having a normal position and including a relatively fixed part, and an adjustable part mounted on said fixed part for adjustment in a certain direction relative to said fixed part, a liquid sampling device mounted on said adjustable part for adjustment with said adjustable part in said certain direction relative to said fixed part and including liquid inlet means having a liquid inlet through which liquid may enter said sampling device, a sample collection chamber for receiving liquid entering through said inlet, and an inlet passage connecting said inlet and said chamber, and wherein said liquid sampling device has an axis, and said base parts include interengaging means for aligning said axis at a fixed angle relative to said certain direction of adjustment of said adjustable part relative to said fixed part in every position of adjustment of said adjustable part relative to said fixed part.

24. Liquid sampling apparatus comprising:

a supporting base having a normal position and including a relatively fixed part and an adjustable part mounted on said fixed part for adjustment in a certain direction relative to said fixed part, and a liquid sampling device mounted on said adjustable part for adjustment with said adjustable part in said certain direction relative to said fixed part and including liquid inlet means having a liquid inlet through which liquid may enter said sampling device, a sample collection chamber for receiving liquid entering through said inlet, and an inlet passage connecting said inlet and said chamber, and wherein said sampling device includes an elongate sample collection tank containing said sample collection chamber, said inlet means are situated at one end of said tank, and said adjustable base part includes means receiving said sample collection tank with the longitudinal axis of the tank extending transverse to said certain direction of adjustment of said adjustable part relative to said fixed part.

25. Liquid sampling apparatus according to claim 24 wherein:

said means receiving said sample collection tank comprises a split sleeve on said adjustable part coaxially and removably receiving said tank, and means for clamping said sleeve about said tank.

26. Liquid sampling apparatus for sampling a liquid flowing through a conduit containing a liquid passage circumferentially bounded by a wall of the conduit, said apparatus comprising:

a liquid sampling device including inlet means having an inlet through which liquid may enter said device, and a liquid collection chamber connected to said inlet means for receiving liquid entering said inlet, and a supporting base supporting said sampling device and including means engagable with the wall of said conduit for securing said sampling device in a fixed position within said conduit.

27. Liquid sampling apparatus according to claim 26 wherein:

said sampling apparatus is adapted to be placed in a generally horizontal conduit through which water flows, said supporting base has a normal position and comprises a dam having upstream and downstream sides, an overflow edge which is generally horizontal and uppermost in said normal position of said base over which water in the conduit can overflow the dam, and an edge portion which extends between and below the ends of said overflow edge in said normal position of said base and is adapted to be sealed to the conduit.

28. Sampling apparatus according to claim 27 wherein:

said sampling device comprises an enlongate sample collection tank containing said sample collection chamber and extending beyond and transverse to said upstream dam side with one end of the tank being located at said upstream side of the dam, and said inlet means is located at said one end of said tank.

29. Sampling apparatus according to claim 27 including:

an inflatable seal extending along and secured to said edge portion of said dam.

30. Liquid sampling apparatus according to claim 26 wherein:

said sampling device includes an elongated tank having a longitudinal axis and containing said sample collection chamber, and said means engagable with the wall of said conduit are disposed circumferentially about said tank for supporting the tank with its longitudinal axis extending longitudinally of the conduit.

31. Liquid sampling apparatus according to claim 30 wherein:

said means engagable with the wall of said conduit comprises clamping means adjustable laterally of said tank.

32. Liquid sampling apparatus for sampling a liquid flowing through a conduit, said apparatus comprising:

a liquid sampling device including inlet means having an inlet through which liquid may enter said device, and a liquid collection chamber connected to said inlet means for receiving liquid entering said inlet, a supporting base supporting said sampling device and including securing means for securing said sampling device in a fixed position within said conduit, and wherein said securing means comprises clamping means adjustable to and from a clamping position wherein said clamping means are disposed for clamping engagement with said conduit, and means for adjusting said clamping means to and from said clamping position.

33. Liquid sampling apparatus for sampling a liquid flowing through a conduit, said apparatus comprising:

a liquid sampling device including inlet means having an inlet through which liquid may enter said device, and a liquid collection chamber connected to said inlet means for receiving liquid entering said inlet, a supporting base supporting said sampling device and including securing means for securing said sampling device in a fixed position within said conduit, and wherein said conduit comprises a pipe, said securing means comprises a resiliently flexible clamp band which is cylindrically curved about an axis of curvature, said clamp band has spaced opposing ends forming a gap between said ends, and means extending between said ends for urging said ends apart to firmly clamp said band within the conduit, and said supporting base further comprises means mounting said sampling device on the inner side of said clamping band opposite said gap.

34. Liquid sampling apparatus according to claim 33 wherein:

said means mounting said sampling device on the inner side of said clamping band comprises a support including a relatively fixed part fixed to the inner side of said band opposite said gap between said band ends and an adjustable part which mounts said sampling device and is adjustable toward and away from said gap.

35. Sampling apparatus according to claim 33 wherein:

said sampling device comprises an enlongate sample collection tank extending substantially parallel to said axis and containing said sample collection chamber, and said inlet means are located at one end of said tank.

36. A liquid sampling device, comprising;

an elongate sample collection tank containing a sample collection chamber and having a longitudinal axis, a circumferential side wall about said axis, and a normal position of use in which said axis is substantially horizontal and a longitudinal portion of said side wall is uppermost, inlet means including a liquid inlet passage through which liquid may enter said chamber, and said inlet passage having an inner end which opens into said chamber and an opposite outer end which opens to the exterior of said tank above said longitudinal side wall portion when said tank occupies said normal position.

37. A liquid sampling device according to claim 36 wherein:

said inlet passage extends through said longitudinal side wall portion of said tank, and said inlet means includes float valve means mounted on said longitudinal side wall portion of said tank for closing said inlet passage when at least one of the following conditions exists: (a) the outer end of said inlet passage is not submerged in liquid, and (b) said sample collection chamber contains a predetermined liquid volume.

38. A method of sampling a liquid flowing through a passage in a generally horizontal conduit having a circumferential wall about said passage, said method comprising the steps of:

providing a liquid sampling device having an inlet through which liquid may enter the device, and a sample collection chamber for receiving liquid entering said inlet, placing said sampling device within said passage in a sampling position wherein said inlet is situated below the liquid level in the conduit, releasably securing said sampling device to said circumferential wall to the conduit to collect a liquid sample, and removing said sampling device from said conduit to retrieve the collected sample.

39. The method of claim 38 including the additional step of:

placing in said conduit downstream of said apparatus a dam which blocks flow through a lower portion of the conduit so as to raise the liquid level upstream of the dam above said inlet.

* * * * *